US006843955B2

United States Patent
Ghosh et al.

(10) Patent No.: US 6,843,955 B2
(45) Date of Patent: Jan. 18, 2005

(54) INJECTION MOLDING OF CERAMIC POWDERS USING NON-GEL FORMING WATER SOLUBLE ORGANIC BINDERS

(75) Inventors: Syamal K. Ghosh, Rochester, NY (US); Donn B. Carlton, Hamlin, NY (US)

(73) Assignee: Eastman Kodak Company, Rochester, NY (US)

( * ) Notice: Subject to any disclaimer, the term of this patent is extended or adjusted under 35 U.S.C. 154(b) by 352 days.

(21) Appl. No.: 09/916,860

(22) Filed: Jul. 27, 2001

(65) Prior Publication Data

US 2001/0050451 A1 Dec. 13, 2001

Related U.S. Application Data

(63) Continuation-in-part of application No. 09/713,518, filed on Nov. 15, 2000.

(51) Int. Cl.[7] .................................................. B28B 1/24
(52) U.S. Cl. ......................... 264/645; 264/669; 264/670
(58) Field of Search ................................. 264/645, 669, 264/670

(56) References Cited

U.S. PATENT DOCUMENTS 5,091,346 A * 2/1992 Inoue et al. .................. 501/93
5,204,296 A * 4/1993 Walter et al. ............... 501/97.1
5,741,833 A * 4/1998 Seyama et al. ............. 523/205
6,008,281 A * 12/1999 Yang et al. ................. 524/322

OTHER PUBLICATIONS

Advanced Ceramic Processing and Technology, Binner, 1990 Chapter 6, Injection Moulding of Fine Ceramics.*

* cited by examiner

Primary Examiner—Christopher A. Fiorilla
(74) Attorney, Agent, or Firm—Stephen H. Shaw

(57) ABSTRACT

A method for compounding gel-free injection molding feed stock for injection molding net-shape ceramic parts, including the steps of: mixing inorganic particles with non-gel forming water soluble organic binders having molecular weight between 1000 and 1,000,000 and that are between 0.5 weight % and 10 weight % based upon the inorganic particles, along with plasticizers, water and processing aids in a mixer to form a mixture, wherein the non-gel forming water soluble organic binders are composed of high and low molecular weight organic binders; compounding the mixed inorganic particles and the non-gel forming water soluble organic binders at a high temperature in the range of between 70° and 98° Centigrade, under shear force, to form a homogenous viscous slurry in the range of $5 \times 10^3$ and $7 \times 10^4$ Pa.sec at a shear rate of 10 $\sec^{-1}$; cooling the homogenous viscous slurry to room temperature to form a compounded solid mass.

17 Claims, 1 Drawing Sheet

INJECTION MOLDING OF CERAMIC POWDERS USING NON-GEL FORMING WATER SOLUBLE ORGANIC BINDERS

CROSS-REFERENCE TO RELATED APPLICATIONS

This is a continuation-in-part of application Ser. No. 09/713,518, filed Nov. 15, 2000, entitled "Injection Molding of Ceramic Powders Using Water Soluble Polymeric Binder" by Syamal K. Ghosh, et al.

FIELD OF THE INVENTION

This invention relates to processes of injection molding of inorganic powders and molding composition thereof. More particularly, the invention concerns low or medium pressure injection molding processes and molding compositions for forming complex net-shape ceramic components. Ceramic powders are compounded with water-soluble organic binders and processing aids. Ceramic powders used in this application are alumina, zirconia-alumina composites and yttria-stabilized tetragonal zirconia.

BACKGROUND OF THE INVENTION

Experience indicates that yttria-alloyed tetragonal zirconia polycrystal (Y-TZP) ceramic offers many advantages over other engineering materials in terms of structural applications. Y-TZP is one of the toughest ceramics known today. Although the toughness is achieved at the expense of hardness and strength, Y-TZP is still far superior to many engineering materials as far as wear, abrasion, and corrosion resistance properties are concerned. Alumina toughened zirconia (ATZ), comprising tetragonal zirconia and alumina is a tough composite ceramic, which potentially can be useful as Y-TZP for many structural applications. These materials, Y-TZP and ATZ, have been successfully used for high precision punches, dies, slitter knives, hydro-dynamic bearings and a multitude of machine components. Unfortunately, high volume manufacturing processes for these materials using conventional dry pressing, gel-casting, or cold isostatic pressing is cost-prohibitive. Also, net-shape production of complex shapes using the above processes is difficult. Injection molding, however, is a process that can be applied to manufacture a large volume of complex shaped parts in a cost-effective way.

Injection molding of fine inorganic powders comprising sub-micron particles, such as Y-TZP, poses many manufacturing problems. It also becomes very difficult to obtain uniform properties of the sintered parts manufactured by an injection molding process if the particle size of powders have a bi-modal distribution. Specifically, ATZ, has a bi-modal particle size distribution. In order to achieve superior properties of Y-TZP, chemically pure zirconia needs to be alloyed with a stabilizing agent(s), and the particle size needs to be maintained at a sub-micron level, preferably at or below 0.3 $\mu$m.

Injection molding complex shaped parts using inorganic powders is not a trivial process. As stated earlier, the injection molding processes for ceramics and metals become extremely challenging when the particle size is in the sub-micron range. Ceramic powders are mixed with primary binders, plasticizers, and processing aids so that a highly viscous material flows to the mold and forms self-supporting solid parts that have sufficient green strength, enabling one to handle them prior to sintering. Improper mixing, along with improper compounding formulation, will cause segregation of the inorganic particles or separation from the organic binder components, as the shear forces act upon the mixture during the injection molding process.

Plasticizers are stable unreactive materials that are added to primary binder(s) to make the compounded product more flexible. Phthalates, adapates, laurates, and oleates are some examples of plasticizers that are compatible with water soluble primary binders. Likewise, a processing aid is added to the binder system to improve the performance during the injection molding process, by modifying the cohesive forces between the binder and ceramic particles. A processing aid reduces the viscosity of the mixture, improves the flow characteristics during molding and eases the release of injection molded parts from the mold. Another important function of a processing aid is to uniformly distribute the binder components throughout the mixture and to enhance the dispersion characteristics of the ceramic particles.

In order to meet some of the requirements of injection molding inorganic powders, preferably ceramic powders having sub-micron particle size, references are made in the prior art whereby compounding, along with mixing, includes adding low melting point wax and some processing aids. Methylcellulose polymers and other high molecular weight polymers are also used as binders in injection molding metallic and ceramic parts. However, such formulations exhibit a multitude of problems in molding complex shape parts. One of the biggest drawbacks with most of the injection molding binder system formulations for metal and ceramic powders is that a lengthy debinding process is necessary to remove the excess binders from the injection molded green parts, prior to sintering, to obtain the finished part. The lengthy debinding step generally includes removing the organic binders, either thermally, or by using chemical solvents. The debinding step may produce a toxic effluent (gas or liquid), thus posing concerns for the environment.

Other binder system formulations described above have not proven to be effective in compounding Y-TZP particles, probably because of the extremely fine particle size associated with Y-TZP. Also, it is difficult to manufacture complex net-shape Y-TZP parts using other formulations because internal cracks and defects often develop during the debinding step. One source of cracking and warping can be attributed to using gel forming material, such as agaroids like agar, agarose and mixtures thereof, in the compounding process.

Consequently, there is a need for an improved method of compounding extremely fine inorganic particles and manufacturing complex net-shaped ceramic parts.

SUMMARY OF THE INVENTION

The need is met according to the present invention by providing a method for compounding gel-free injection molding feed stock for injection molding net-shape ceramic parts, including the steps of:

a) mixing inorganic particles with non-gel forming water soluble organic (sometimes referred to as polymer) binders having molecular weight between 1000 and 1,000,000 and that are between 0.5 weight % and 10 weight % based upon the inorganic particles, along with plasticizers, water and processing aids in a mixer to form a mixture, wherein the non-gel forming water soluble organic binders are composed of high and low molecular weight organic binders, and wherein a weight fraction of the high molecular weight organic binders with respect to the low molecular weight organic binders varies between 0.1 and 0.6;

b) compounding the mixed inorganic particles and the non-gel forming water soluble organic binders at a high temperature in the range of between 70° and 98° Centigrade, under shear force, to form a homogenous viscous slurry in the range of $5 \times 10^3$ and $7 \times 10^4$ Pa.sec at a shear rate of 10 sec$^{-1}$;

c) cooling the homogenous viscous slurry to room temperature to form a compounded solid mass;

d) grinding the compounded solid mass to small pellets to provide feed stock for an injection molding machine;

e) injection molding the feedstock to produce a green component for subsequent drying; and f) sintering to form a net-shape final product.

ADVANTAGES

This invention overcomes many of the problems that are associated with injection molding processes for metals and ceramics. The advantages of the present invention include:

A very cost-effective method of injection molding submicron particle sized ceramic powders.

A very cost-effective method of producing large quantities of defect-free net-shape complex ceramic parts.

Reducing the overall manufacturing time and cost by eliminating a lengthy debinding step.

Injection molding is carried out at high solids loading.

Elimination of the aforementioned debinding step enables this process to be considered environmentally friendly because there is not a need for handling toxic effluent gases or liquids.

Since water is used as a solvent for the organic binders the injection molding and the sintering process are environmentally friendly.

Since the compounding was not accomplished by a gelation process and the binders are not as hygroscopic as agar (polysaccharides), the drying step after injection molding does not cause any warping or cracking.

DETAILED DESCRIPTION OF THE INVENTION

Figure 1:
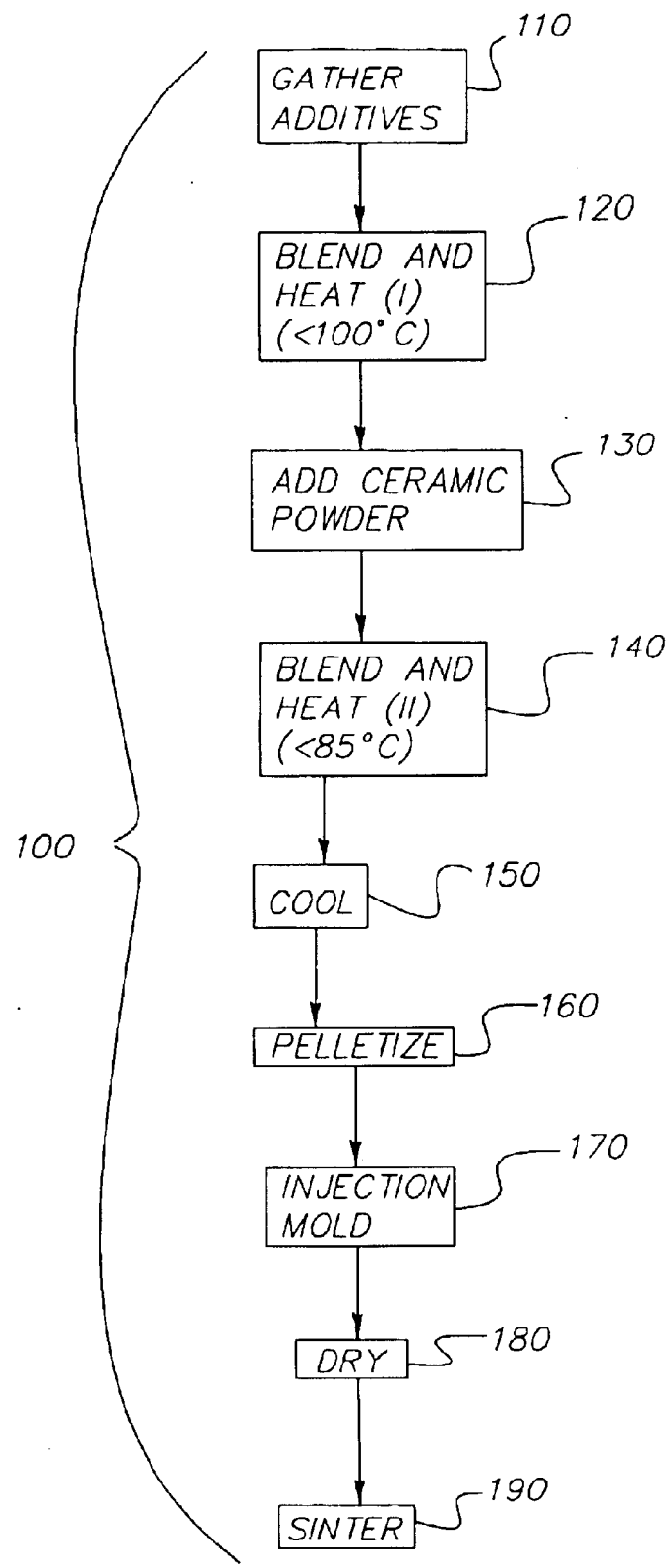
FIG. 1 is a flowchart showing one embodiment of the method of injection molding in accordance with the present invention.

This invention generally relates to a method of producing gel-free, feedstock for injection molding complex, net-shape ceramic parts. In other words, no gel forming material is used herein, in order to reduce the likelihood of warping and cracking of the net-shape ceramic parts. One source of cracking and warping can be attributed to using gel forming material, such as agaroids or polysaccharides like agar, agarose, and mixtures thereof, in the compounding process.

As used herein the term ceramic powder is intended to include, without limitation, powders of inorganic materials such as oxides, borides, nitrides, carbides, and silicides; powders of metals and non-metals; or mixtures thereof. More particularly, this invention relates to a method of injection molding yttria-alloyed zirconia crystal ceramics (Y-TZP) having average particle size 0.3 µm, and alumina toughened zirconia ceramics (ATZ), comprising particles ranging from 0.3 to 1.0 µm, and having bi-modal distribution. According to the process of this invention, the compounding method involves mixing inorganic particles, for example, ceramic powders, with binder components comprising non-gel forming water soluble primary organic binders, plasticizers, water, and processing aids. Non-gel forming water soluble primary organic binders are defined as polymers which dissolve in water at a temperature range between room temperature (22° C.) and 98° C., and that are non-gel forming. The selected organic binders have a molecular weight distribution which ranges from 1,000 to 1,000,000. Organic binders having molecular weight between 1,000 and 100,000 are arbitrarily defined as "low molecular weight" binders. Similarly, organic binders having molecular weight between 100,001 and 1,000,000 are arbitrarily defined as "high molecular weight" binders. High molecular weight binders provide higher green strength to the injection molded ceramic parts. Low molecular weight binders may also be used to provide more uniform and easier mixing, and aid in controlling the viscosity of the slurry during the compounding process. The viscosity of the compounded slurry can also be controlled by using proper plasticizers and processing aids. The weight fraction of the high molecular weight organic binders with respect to the low molecular weight organic binders varies between 0.1 and 0.6.

The water soluble mixture of organic binders is provided in an amount between about 0.5 weight % and about 10 weight % based upon the inorganic solids, i.e., ceramic powders, in the compounding mixture. Most preferably, the primary organic binders comprise between about 3% and 8% by weight of inorganic solids in the compounding mixture. Although higher amounts of organic binders do not have any adverse effect on the injection molding process, it has been observed that higher than 8% by weight may cause problems during the sintering process.

Water is added as a liquid carrier to the mixture to produce a homogeneous slurry having a viscosity necessary to make the slurry amenable to being molded by a desired molding process. Ordinarily, water is added in an amount that is necessary to produce a homogeneous slurry and also to make sure that the proper viscosity of the slurry is maintained. Generally, the amount of water added is between about 30% and about 50% by weight of the mixture; preferably, the amount of water is between 35% and 45% by weight of the mixture.

The mixing is done at a relatively high temperature, ranging between 70° and 98° Centigrade, under a high shear condition using a Ross shear mixer that provides shear force. The shearing action is necessary to produce compounded ceramic powders with high solids loading in a uniform and dispersed state. This is highly desirable for the subsequent injection molding process. Use of a composition with high solids loading necessitates the elimination of the debinding step. Use of compositions with high solids loading results in lower shrinkage when the injection molded parts are sintered, facilitating more stringent dimensional control and mitigating the potential for developing cracks during a densification (i.e., sintering) process. The benefits afforded by this sintering process include higher yields and better control on producing net shape parts. This sintering process can have a significant impact on the cost of the overall injection molding process.

Mixing under high shear produces a homogenous viscous slurry. Viscosity of the slurry, measured at approximately 80° Centigrade, is maintained between $5 \times 10^3$ and $7 \times 10^4$ Pa.sec at a shear rate of 10 sec$^{-1}$. The viscosity depends on the shear rate, volume percentage of ceramic, mixing temperature, and the chemical structure of the binders and processing aids. In general, the slurry's viscosity at this high temperature, around 80° C., will have a dough-like consistency and be gel-free. Mixing time generally varies between 4 and 12 hours so that a uniform and homogenous mixture is obtained. The homogeneous viscous slurry is then cooled to room temperature to form a compounded solid mass and shredded to form pellets to provide feedstock for the subsequent injection molding process in a conventional injection molding machine, the details of which are described below. Alternatively, the viscous slurry, after thorough mixing, could be granulated before cooling, as for example, by passing the viscous material directly through an extruder and cutting the extrudate as it exits the die.

Referring to FIG. 1, a flow chart of a ceramic powder compounding and injection molding process, according to the present invention, is illustrated. The injection molding process 100 includes the steps of gathering compounding additives of a binder system having a mixture of primary organic binders, plasticizers, processing aids, and water. The compounding additives are added together and placed in a mixer in step 110, a small quantity of water is added, stirred gently, and heated to a maximum of 98° C. Next, the compounding additives are blended in the mixer (e.g. Ross, model #LDM-2) until all the additives are dissolved and intimately mixed to form a solution in a process of blending and heating step I, shown herein as process step 120. Next, either a single or multiple species of ceramic powders are added, along with some additional water, to the thoroughly mixed binder system in process step 130. Generally, the amount of ceramic powder in the mixture is between about 60 and 95% by weight of the organic binder components. Preferably, the ceramic powder constitutes between about 80% and 95% by weight of the binder components, and most preferably constitutes between about 85% and 95% by weight of the binder components. Subsequently, the temperature of the mixer is lowered to a range of 70° to 90°, preferably to 85° C., and blended for at least 4 to 12 hours, preferably 6 hours in blending and heating step II, shown herein as process step 140; and the slurry is cooled to room temperature, approximately 20–23° C., in step 150. The cooled compounded solid ceramic mix is then shredded to small pieces in step 160 to provide feedstock for the next injection molding process. The injection molding step 170 can be carried out in a conventional injection molding machine, for example, a machine manufactured by Boy, model #22M. The injection molded green ceramic parts are dried carefully so that the parts do not warp because of non-uniform drying in step 180. The dried green parts are sintered at 1400° to 1600° C. or preferably at 1500° C. for at least 2 hours in step 190.

WORKING EXAMPLES

1. Zirconia powder alloyed with yttria (3 mole %) were mixed with a non-gel forming water soluble binder system to form a slurry. The following compounding formulation was used to make up the feedstock for the injection molding process:

| | |
|---|---|
| 3000 g | Y-TZP powder |
| 60 g | poly(ethylene oxide), M.W. (molecular weight) 900,000 |
| 30 g | polyvinylalcohol, M.W. 115,000 |
| 60 g | polystyrene sulfonate, M.W. 70,000 |
| 30 g | hydroxypropyl cellulose, M.W 60,000 |
| 60 g | stearic acid |
| 60 cc | n-propyl oleate |
| 60 cc | diisononyl adipate |
| 20 cc | Menhaden fish oil |
| 1200 cc | distilled water |

The inorganic particles, Y-TZP, have an average particle size that can range from 0.2 to 0.5 µm. The binder system includes primary binders such as poly(ethylene oxide), polyvinyl-alcohol, polystyrene sulfonate, and hydroxypropyl cellulose. The weight fraction of high molecular weight to low molecular weight primary binders is 0.5. The primary binders are mixed with plasticizers n-propyl oleate and diisnonyl adipate, and processing aids, such as stearic acid and Menhaden fish oil, and thoroughly mixed with 500 cc of distilled water at 95° C. and blended for at least 2 hours, preferably for 4 hours. Zirconia powder (Y-TZP) is then added to the binder system and blended at 85° C. for at least 4 hours while adding water occasionally to maintain a slurry-like consistency, having a viscosity around $1 \times 10^4$ Pa.sec at a shear rate of $10 \sec^{-1}$. The compounded slurry is allowed to cool to room temperature to form a solid mass and subsequently shredded to small pieces as injection molding feedstock. In general, the weight percentage of ceramic powder is approximately 60 to 90%. In other words, the solid loading is in the range of around 60 to 90% by weight in relation to all binders and organic additives that are added for the compounding process. In this example, the solid loading is around 87% by weight.

2. ATZ powder comprising 20% by weight alumina and 80% by weight Y-TZP is mixed with a non-gel forming water soluble binder system to form a slurry. The following compounding formulation was used to provide feedstock for the subsequent injection molding process:

| | |
|---|---|
| 3000 g | ATZ powder (20% alumina, 80% zirconia, by weight) |
| 30 g | polyvinylalcohol, MW. 10,000 |
| 40 g | poly(ethylene oxide), M.W. 900,000 |
| 60 g | polystyrene sulfonate, M.W. 70,000 |
| 120 cc | oleic acid |
| 60 cc | n-propyl oleate |
| 60 cc | diisononyl oleate |
| 60 g | stearic acid |
| 1200 cc | distilled water |

ATZ can constitute alumina anywhere between 5%–49% by weight, and have an average particle size from 0.2 to 1.0 µm. The binder system includes the primary binders poly (ethylene oxide), polyvinylalcohol, and a sodium derivative of polystyrene sulfonate. The weight fraction of high molecular weight to low molecular weight primary binders is 0.44. The primary binders are mixed with plasticizers n-propyl oleate and diisnonyl adipate, and processing aid stearic acid, thoroughly mixed with 500 cc of distilled water at 95° C. and blended for at least 2 hours, preferably for 4 hours. ATZ powder is then added to the binder system and blended at 85° C. for at least 4 hours while adding water occasionally to maintain a slurry-like consistency, having viscosity around $7 \times 10^4$ Pa.sec at a shear rate of $10 \sec^{-1}$. The compounded slurry is allowed to cool to room temperature to form a solid mass and subsequently shredded to small pieces as injection molding feedstock. The weight percentage of ceramic powder is 95.67% compared to primary binders. The solid loading for the ceramic powder is around 86% by weight.

3. Zirconia powder alloyed with yttria (3 mole %) were mixed with a non-gel forming water soluble binder system to form a slurry. The following compounding formulation was used to make up the feedstock for the injection molding process:

| | |
|---|---|
| 3000 g | Y-TZP powder |
| 50 g | poly(ethylene oxide), M.W. (molecular weight) 900,000 |
| 30 g | poly(ethylene glycol), M.W. 20,000 |
| 30 g | methyl vinyl ether/meleic anhydride copolymer, M.W. 70,000 |
| 40 g | polystyrene sulfonate, M.W 70,000 |
| 60 g | stearic acid |
| 60 cc | n-propyl oleate |
| 60 cc | diisononyl adipate |
| 20 cc | Menhaden fish oil |
| 1200 cc | distilled water |

The inorganic particles, Y-TZP, have an average particle size that can range from 0.2 to 0.5 µm. The binder system includes primary binders such as poly(ethylene oxide), poly(ethylene glycol), methyl vinyl ether/maleic anhydride copolymer, and polystyrene sulfonate. The weight fraction of high molecular weight to low molecular weight primary binders is 0.5. The primary binders are mixed with plasticizers n-propyl oleate and diisonyl adipate, and processing aids, such as stearic acid and Menhaden fish oil, thoroughly mixed with 500 cc of distilled water at 95° C. and blended for at least 2 hours, preferably for 4 hours. Zirconia powder (Y-TZP) is then added to the binder system and blended at 85° C. for at least 4 hours while adding water occasionally to maintain a slurry like consistency, having viscosity around $3\times10^4$ Pa.sec at a shear rate of 10 sec$^{-1}$. The compounded slurry is allowed to cool to room temperature to form a solid mass and subsequently shredded to small pieces as injection molding feedstock. The weight percentage of primary binder compared to that of ceramic powder is 5%. The solid loading is approximately 88.5% by weight.

4. The shredded feedstock from Examples 1, 2, and 3 were fed in to an injection molding machine (Boy, Model #22M) to form parts having various geometric configurations. The following are some typical injection molding parameters:

| | |
|---|---|
| clamp pressure: | 150 bar |
| injection pressure | 80 bar |
| molding temperature | 70° C. |

The injection molded green ceramic parts were air dried at ambient temperature, and sintered at 1500° C. for 2 hours. The sintered parts had greater than 99.5% theoretical density.

The final result is a homogenous mass with a specific workable density, and mechanical and chemical properties that will allow practical injection molding.

The invention has been described with reference to a preferred embodiment; However, it will be appreciated that variations and modifications can be effected by a person of ordinary skill in the art without departing from the scope of the invention.

PARTS LIST 100 injection molding process
110 gathering additives step
120 blending and heating step I
130 adding ceramic powder step
140 blending and heating step II
150 cooling step
160 pelletizing step
170 injection molding step
180 drying step
190 sintering step

What is claimed is:

1. A method for forming an injection molded sintered ceramic parts, comprising the steps of:
   a) mixing inorganic particles with non-gel forming water soluble organic binders having molecular weight between 1000 and 1,000,000 to form a mixture, wherein the organic particles weigh between 0.5% and 10% of the mixture including plasticizers, water and processing aids in a mixer, wherein the non-gel forming water soluble organic binders are composed of high and low molecular weight organic binders, and wherein a weight fraction of the high molecular weight organic binders with respect to the low molecular weight organic binders varies between 0.1 and 1.6;
   b) compounding the mixed inorganic particles and the non-gel forming water soluble organic binders at a high temperature in the range of between 70° and 98° Centigrade, under shear force, to form a homogenous viscous slurry in the range of $5\times10^3$ and $7\times10^4$ Pa.sec at a shear rate of 10 sec$^{-1}$;
   c) cooling the homogenous viscous slurry to room temperature to form a compounded solid mass;
   d) grinding the compounded solid mass to small pellets to provide feed stock for an injection molding machine;
   e) injection molding the feedstock to produce a green part;
   f) drying the green part at ambient temperature to form a dried green part; and
   g) sintering the dried green part to form an injection molded ceramic part.

2. The method claimed in claim 1, wherein the inorganic particles are Y-TZP ceramic comprising 3 mole % yttria, and have an average particle size ranging from 0.2 to 0.5 µm.

3. The method claimed in claim 1, wherein the inorganic particles are ceramic composite alumina-toughened zirconia, comprising between 15% to 49% by weight of alumina, and have average particle size ranging from 0.2 to 1.0 µm.

4. The method claimed in claim 1, wherein the inorganic particles comprises between about 45% to 90% by weight of the compounded mixture.

5. The method claimed in claim 1, further comprising the step of mixing and heating the water soluble organic binders, plasticizers and water to a temperature between 90–98° C. prior to adding the inorganic particles, and decreasing the temperature to a range of 70–90° C. after adding the inorganic particles and mixing for more than 4 hours in a shear mixer.

6. The method claimed in claim 1, wherein the homogenous viscous slurry is obtained between 4 and 12 hours.

7. The method claimed in claim 1, wherein the water in the mixture is between 30% and 50% by weight of the mixture, and preferably between 35% and 45% by weight of the mixture.

8. The method claimed in claim 1, wherein the non-gel forming water soluble organic binders are between 3% and 8% by weight of the inorganic particles.

9. An injection molding process, comprising the steps of:
   a) mixing ceramic powders with non-gel forming water soluble organic binders having molecular weight between 1000 and 1,000,000 to form a mixture, wherein the inorganic particles weigh between 0.5% and 10% of the mixture including plasticizers, water and processing aids in a mixer, wherein the non-gel forming water soluble organic binders are composed of high and low molecular weight organic binders, and wherein a weight fraction of the high molecular weight organic binders with respect to the low molecular weight organic binders varies between 0.1 and 0.6;

b) compounding the mixed ceramic powders at high temperature in the range of between 70° and 98° Centigrade, under shear force, to form a homogenous viscous slurry in the range of $5 \times 10^3$ and $7 \times 10^4$ Pa.sec at a shear rate of 10 $sec^{-1}$;

c) cooling the homogenous viscous slurry to room temperature to form a compounded solid mass;

d) grinding the compounded solid mass to small pellets to provide feed stock for an injection molding machine; and e) injection molding the feedstock to produce a green part.

10. The process claimed in claim 9, wherein the ceramic powders are Y-TZP ceramic comprising 3 mole % yttria, and have an average particle size ranging from 0.2 to 0.5 μm.

11. The process claimed in claim 9, wherein the ceramic powders are ceramic composite alumina-toughened zirconia, comprising between 5% to 49% by weight of alumina, and have average particle size ranging from 0.2 to 1.0 μm.

12. The process claimed in claim 9, wherein the ceramic powders comprise between about 45% to 90% by weight of the compounded mixture.

13. The process claimed in claim 9, further comprising the step of mixing and heating the non-gel forming water soluble organic binders, plasticizers and water to a temperature between 90 to 98° C. prior to adding the ceramic powders, and decreasing the temperature to a range of between 70–90° C. after adding the ceramic powders and mixing for more than 4 hours in a shear mixer.

14. The process of claim 9, wherein the non-gel forming water soluble organic binders include primary binders poly (ethylene oxide), polyvinyl-alcohol, polystyrene sulfonate and its derivatives, hydroxypropyl cellulose, methyl vinyl ether/meleic anhydride copolymer, poly (ethylene glycol) or a mixture thereof.

15. The process of claim 9, wherein the non-gel forming water soluble organic binders are between 3% and 8% by weight of the ceramic powders.

16. The process of claim 9, wherein the water in the mixture is between 30% and 50% by weight of the mixture, and preferably between 35% and 45% by weight of the mixture.

17. The process of claim 9 wherein the homogenous viscous slurry is obtained between 4 and 12 hours.

* * * * *